(12) United States Patent
Jönsson et al.

(10) Patent No.: US 9,512,454 B2
(45) Date of Patent: Dec. 6, 2016

(54) METHODS FOR IMPROVEMENT OF ENZYMATIC HYDROLYSIS OF LIGNOCELLULLOSIC MATERIAL

(75) Inventors: Leif Jönsson, Umea (SE); Björn Alriksson, Örnsköldsvik (SE); Venkata Prabhakar Soudhama, Örnsköldsvik (SE)

(73) Assignee: Sekab E-Technology AB, Örnsköldsvik (SE)

( * ) Notice: Subject to any disclaimer, the term of this patent is extended or adjusted under 35 U.S.C. 154(b) by 36 days.

(21) Appl. No.: 14/123,556

(22) PCT Filed: Jun. 11, 2012

(86) PCT No.: PCT/EP2012/061021
§ 371 (c)(1),
(2), (4) Date: Feb. 24, 2014

(87) PCT Pub. No.: WO2013/000696
PCT Pub. Date: Jan. 3, 2013

(65) Prior Publication Data
US 2014/0154746 A1 Jun. 5, 2014

(30) Foreign Application Priority Data
Jun. 30, 2011 (EP) .................................. 11172123

(51) Int. Cl.
| | | |
|---|---|---|
| *C12P 7/62* | (2006.01) | |
| *C12P 19/14* | (2006.01) | |
| *C12P 7/10* | (2006.01) | |
| *C12P 19/02* | (2006.01) | |
| *C12P 19/04* | (2006.01) | |
| *C12P 19/16* | (2006.01) | |
| *C08B 1/00* | (2006.01) | |

(52) U.S. Cl.
CPC .................. *C12P 19/14* (2013.01); *C08B 1/00* (2013.01); *C12P 7/10* (2013.01); *C12P 19/02* (2013.01); *C12P 19/04* (2013.01); *C12P 19/16* (2013.01); *C12P 2201/00* (2013.01); *C12P 2203/00* (2013.01); *Y02E 50/16* (2013.01)

(58) Field of Classification Search
None
See application file for complete search history.

(56) References Cited

FOREIGN PATENT DOCUMENTS

WO WO 2005/099854 A1 10/2005

OTHER PUBLICATIONS

Larsson et al., Applied Biochemistry and Biotechnology, 1999, vol. 77-79, p. 91-103.*
Cheng et al., Appl. Biochem. Biotechnol., 2010, vol. 162, p. 1768-1784.*
Stenberg et al., J. Chem. Technol. Biotechnol., 1998, vol. 71, p. 299-308.*
R. C. Sun "Cereal Straw as a Resource for Sustainable Biomaterials and Biofuels: Chemistry, Extractives, Lignins, Hemicelluloses and Cellulose", Elsevier, Jan. 18, 2010—Technology & Engineering, pp. 270, 274 and 275 Only.*
Akaracharanya et al., "Evaluation of the waste from cassava starch production as a substrate for ethanol fermentation by *Saccharomyces cerevisiae*," Ann. Microbiol. 61:431-436 (2011).
Alriksson et al., "Ammonium hydroxide detoxification of spruce acid hydrolysates," Appl. Biochem. Biotechnol. 121-124:911-922 (2005).
Alriksson et al., "Optimal conditions for alkaline detoxification of dilute-acid lignocellulose hydrolysates," Appl. Biochem. Biotechnol. 129-132:599-611 (2005).
Alvira et al., "Pretreatment technologies for an efficient bioethanol production process based on enzymatic hydrolysis: a review," Bioresource Technol. 101:4851-4861 (2010).
Harmsen et al., "Literature review of physical and chemical pretreatment processes for lignocellulosic biomass," pp. 1-48 (2010), retrieved from the internet on Oct. 19, 2011, http://www/biomassmandbioenergy.nl/filesdwnld/Literature%20review_FBR.pdf.
Cantarella et al., "Comparison of different detoxification methods for steam-exploded poplar wood as a substrate for the bioproduction of ethanol in SHF and SSF," Process Biochem. 1533-1542 (2004).
Palmqvist et al., "Fermentation of lignocellulosic hydrolysates. I: inhibition and detoxification," Bioresource Technol. 74:17-24 (2000).
Pan et al., "Strategies to enhance the enzymatic hydrolysis of pretreated softwood with high residual lignin content," Appl. Biochem. Biotechnol. 121-124:1069-1079 (2005).
Saha et al., "Dilute acid pretreatment, enzymatic saccharification, and fermentation of rice hulls to ethanol," Biotechnol. Prog. 21:816-822 (2005).
Soudham et al., Reducing agents improve enzymatic hydrolysis of cellulosic substrates in the presence of pretreatment liquid, J. Biotechnol. 155:244-250 (2011).
International Search Report for PCT/EP2012/061021 mailed Jul. 30, 2012.
International Preliminary Report on Patentability for PCT/EP2012/061021 mailed Aug. 8, 2013.
Aden et al., "Lignocellulosic Biomass to Ethanol Process Design and Economics Utilizing Co-Current Dilute Acid Prehydrolysis and Enzymatic Hydrolysis for Corn Stover," Chapter 1.2: Process Overview, Internet Citation, Jun. 1, 2002 (Jun. 1, 2002), pp. 5-6, URL:http://www.osti.gov/bridge/servlets/purl/15001119-zb17aV/native/15001119.pdf [retrieved on Aug. 5, 2009].

(Continued)

*Primary Examiner* — Kade Ariani
(74) *Attorney, Agent, or Firm* — Myers Bigel, P.A.

(57) ABSTRACT

The present invention relates to a method of enzymatic hydrolysis of a lignocellulosic material, comprising the steps of: a) pretreating the lignocellulosic material to obtain a slurry having a pH of less than 6; b) adding NaOH, $Ca(OH)_2$ and/or CaO to the slurry to increase its pH to at least 8, said addition being carried out at a slurry temperature of at least 60° C.; c) reducing the pH of the slurry to below 7; and optionally cooling the slurry from step b) to a temperature below 60° C.; and d) adding hydrolytic enzymes to the slurry from c) and allowing the slurry to hydrolyze wherein no washing of the slurry is performed prior to step d).

19 Claims, 1 Drawing Sheet

(56) References Cited

OTHER PUBLICATIONS

Alriksson et al., "Optimal conditions for alkaline detoxification of dilute-acid lignocellulose hydrolysates," *Appl. Biochem. Biotechnol.* 129-132:599-611 (2006).
Kumar et al. "Impact of pretreatment and downstream processing technologies on economics and energy in cellulosic ethanol production", *Biotechnology for Biofuels* 4:27 pp. 1-19 (2011).
Millati et al. "Effect of pH, time and temperature of overliming on detoxification of dilute-acid hydrolyzates for fermentation by *Saccharomyces cerevisiae*", *Process Biochemistry* 38:515-522 (2002).
Extended European Search Report corresponding to European Application No. 15168676.3 dated Sep. 1, 2015.

\* cited by examiner

METHODS FOR IMPROVEMENT OF ENZYMATIC HYDROLYSIS OF LIGNOCELLULLOSIC MATERIAL

RELATED APPLICATIONS

This application is a 35 U.S.C. §371 national phase application of PCT Application PCT/EP2012/061021, filed Jun. 11, 2012, which claims priority to EP 11172123.9, filed Jun. 30, 2011. The entire content of each of these applications is incorporated herein by reference.

TECHNICAL FIELD

The present invention relates to improvements of the enzymatic hydrolysis in saccharification of a pretreated lignocellulosic material. The method provides sugars which are useful as substrates in the manufacture of various target compounds. The method is inter alia useful in the manufacture of a fermentation product, such as ethanol, from the lignocellulosic material.

BACKGROUND

Biorefineries producing commodities from renewable resources offer an alternative to oil refineries based on dwindling supplies of petroleum and permit a move towards improved energy security. Lignocellulosic materials from forestry and agriculture are attractive as feedstocks, since they are abundant, relatively inexpensive, and are not used for food. Lignocellulose consists mainly of lignin and two classes of polysaccharides, cellulose and hemicellulose. The polysaccharides can be hydrolyzed to sugars and converted to various fermentation products, such as bioalcohols, in processes based on biocatalysts, such as the industrially important baker's yeast (*Saccharomyces cerevisiae*).

The hydrolysis of cellulose may be preceded by a pretreatment, in which the hemicellulose is degraded and the cellulose is made increasingly accessible to cellulolytic enzymes or acidic hydrolysis, see e.g. Alvira et al and Harmsen et al.

By using enzymatic hydrolysis, hydrolysis and fermentation can be performed simultaneously in a simultaneous saccharification and fermentation (SSF) process or in a consolidated bioprocess (CBP). Alternatively, separate hydrolysis and fermentation (SHF) can be used, a process configuration that may also include enzyme-based hydrolysis of the cellulose.

SUMMARY

In order to obtain high yields of sugars from lignocellulosic substrates, the inventors consider dilute acid hydrolysis pretreatment and/or steam pretreatment with acid catalysts to be appropriate pretreatment methods. Furthermore, the inventors have realized that in industrial processes for converting lignocellulosic biomass to fermentation products, such as cellulosic ethanol, the whole slurry obtained after pretreatment will probably be used at a high solids concentration. However, the pre-treatment liquid is known to inhibit enzymatic hydrolysis. Previously, addition of surfactants has been considered for improving enzymatic saccharification of cellulosic substrates. Surfactants probably prevent unproductive binding of enzymes to complex lignocellulosic substrates, such as pretreated wood. The economical benefit of adding surfactants to reaction mixtures intended for production of yield-sensitive low value-added products such as liquid biofuels has, however, been questioned.

The addition of enzymes constitutes a considerable part of the total cost for the process of producing products from lignocellulosic material. The cost for enzymes is for instance regarded as one of the main obstacles for industrial implementation for conversion of lignocellulose to liquid biofuels. It would therefore be desirable to improve the efficiency of the enzymatic hydrolysis of lignocellulosic materials, e.g. to obtain more sugars from a certain enzyme dosage and time period, or to obtain the same amount of sugars from a lower enzyme dosage for the same time period. It is also desirable to achieve a certain amount of sugars with a certain enzyme dosage in a shorter time period, since this increases the production capacity and thereby allows for improved production and/or decreased costs of investment. Improving the efficiency of the enzymatic hydrolysis of cellulose may significantly contribute to commercialization of products based on lignocellulose-derived sugars.

It is an object of some aspects of the invention to improve the efficiency or production capacity of enzymatic hydrolysis of lignocellulosic materials. For this and other objects that will be evident to a person skilled in the art from the following disclosure, the present invention provides according to a first aspect a method of enzymatic hydrolysis of a lignocellulosic material, comprising the steps of:
  a) pretreating the lignocellulosic material to obtain a slurry having a pH of less than 6,
  b) adding NaOH, $Ca(OH)_2$ and/or CaO to the slurry to increase its pH to at least 8, said addition being carried out at a slurry temperature of at least 60° C.;
  c) reducing the pH of the slurry to below 7; and optionally cooling the slurry from step b) to a temperature below 60° C. and
  d) adding hydrolytic enzymes to the slurry from c) and allowing the slurry to hydrolyze.

The present invention further provides according to a second aspect a method of enzymatic hydrolysis of a lignocellulosic material, comprising the steps of:
  a) pretreating the lignocellulosic material using $SO_2$ and/or sulfurous acid to obtain a slurry having a pH of less than 5;
  b) adding $Ca(OH)_2$ and/or CaO to the slurry to increase its pH to at least 8;
  c) reducing the pH of the slurry from step b) to below 7; and
  d) adding hydrolytic enzymes to the slurry from c) and allowing the slurry to hydrolyze.

According to a third aspect the present invention relates to a method of producing at least one target molecule comprising the steps of:
  a) pretreating a lignocellulosic material to obtain a slurry having a pH of less than 6;
  b) adding Na(OH), $Ca(OH)_2$ and/or CaO to the slurry to increase its pH to at least 8;
  c) reducing the pH of the slurry to below 7;
  d) adding hydrolytic enzymes to the slurry from c) and subjecting the slurry to enzymatic hydrolysis to obtain an at least partly hydrolyzed slurry.
  e) utilizing the at least partly hydrolyzed slurry from step d) as a substrate in a fermentation process for production of at least one fermentation product;
  wherein the enzymatic hydrolysis in step d) and the fermentation process in step e) is performed separately in a separate hydrolysis and fermentation process.

In a fourth aspect the present invention further provides a novel use of NaOH, Ca(OH)$_2$ or CaO for improving enzymatic hydrolysis of a lignocellulose-derived slurry derived from dilute acid pretreatment.

DETAILED DESCRIPTION

Figure 1A:
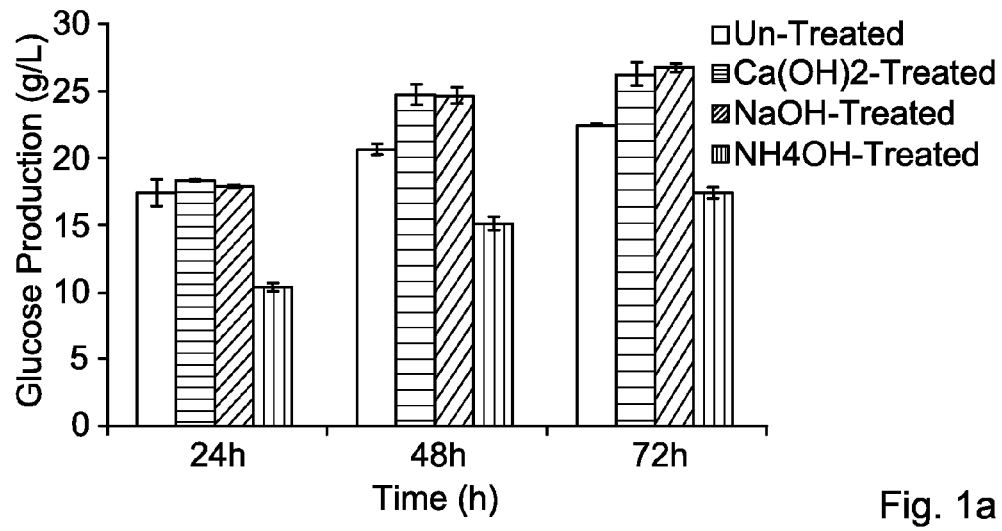
FIG. 1a:
The Y-axis shows the glucose production (g/l) during 72 h of enzymatic hydrolysis of alkali-treated and untreated spruce slurry. The treatment conditions were: NH4OH, pH 9, 55° C., 3 h; NaOH, pH 9, 80° C., 3 h; Ca(OH)2, pH 11, 30° C., 3 h. The error bars show the standard deviations of four measurements.

The present invention is based on the finding that enzymatic hydrolysis of cellulosic substrates in the presence of the liquid fraction obtained after pretreatment of a lignocellulose material can be enhanced by certain alkaline treatments. This approach differs from using alkaline treatment to achieve improved fermentability of lignocellulose hydrolysates (described in for example Alriksson et al 2005 and Alriksson et al 2006) since the target in the latter case is to alleviate the effect of inhibitors on the fermenting microorganism and not, as disclosed herein, on improving the enzymatic hydrolysis. Therefore, according to a first aspect, the inventions relates to a method of enzymatic hydrolysis of a lignocellulosic material, comprising the steps of:
a) pretreating the lignocellulosic material to obtain a slurry having a pH of less than 6,
b) adding Na(OH), Ca(OH)$_2$ and/or CaO to the slurry to increase its pH to at least 8, said addition being carried out at a slurry temperature of at least 60° C.;
c) reducing the pH of the slurry to below 7; and optionally cooling the slurry from step b) to a temperature below 60° C. and
d) adding hydrolytic enzymes to the slurry from step c) and allowing the slurry to hydrolyze.

In step a), the lignocellulosic material is subjected to a pretreatment, in which the hemicellulose is degraded and the cellulose is made increasingly accessible to cellulolytic enzymes. The pretreatment may involve one or several pretreatment methods known to the skilled person. As an example, the pretreatment may be performed at elevated temperature with acid, typically dilute mineral acid, such as sulfuric acid. The pre-treatment may involve impregnation, which refers to impregnation of the cellulosic material with an impregnation fluid, followed by heating. In the case of acid pretreatment, the impregnation fluid may be an acid solution, such as a mineral acid solution. The impregnation may also be performed with a gas, such as a SO$_2$ gas or CO$_2$ gas, or with the combination of a gas with a liquid to obtain e.g. sulfurous acid or carbonic acid. The elevated temperature may be achieved by steaming, a process used to drive air out from the cellulosic biomass to facilitate hydrolysis of the cellulose. Steaming is a well-known method for pretreating e.g. lignocellulosic biomass. As another example, the pretreatment may involve steam explosion, a process that combines steam, hydrolysis and rapid pressure releases for rupturing cellulosic fibers. However, the method of enzymatic hydrolysis according to the invention is especially suitable on lignocellulosic material subjected to dilute acid pretreatment since the effects of the alkaline treatment is most pronounced in this case. Therefore in one preferred embodiment the pretreatment in step a) is dilute acid pretreatment. The pH of the slurry obtained in step a) will depend on the pretreatment. Anyway, it is less than 6 according to the first aspect. In one embodiment, the pH of the slurry obtained in step a) is less than 5, such as less than 4, such as less than 3, such as less than 2. If the pretreatment is dilute acid pretreatment the pH of the slurry obtained in step a) would typically be in the range of 1 to 3. Therefore, in one embodiment the pH of the slurry obtained in step a) is in the range of pH 1.0 to 3.0.

In step b) Na(OH), Ca(OH)$_2$ and/or CaO is added to the slurry to increase its pH to at least 8. An increase of the pH to at least 8.0 is sufficient to improve the enzymatic hydrolysis. The hydrolysis may however be even further improved if Na(OH), Ca(OH)$_2$ and/or CaO is added to the slurry such that the pH of the slurry is increased further, such as for example to pH 9.0. Therefore, in one embodiment the pH of the slurry in step b) is increased to at least 8.5 preferably to at least 9.0. In one embodiment the pH of the slurry in step b) is increased to at least 8.0 but not above pH 12.0.

The present inventors have further demonstrated that, by having a relatively high temperature of the slurry in step b) prior to addition of Na(OH), Ca(OH)$_2$ and/or CaO, a smaller increase in pH is needed compared to the case when the slurry temperature is below 60° C. Thereby less Na(OH), Ca(OH)$_2$ and/or CaO can be used in step b) which makes the method cheaper. If the slurry temperature is further increased the amount of added Na(OH), Ca(OH)$_2$ and/or CaO can be even further reduced without reducing the efficiency of the hydrolysis. Therefore, in a preferred embodiment the addition of Na(OH), Ca(OH)$_2$ and/or CaO in step b) is being carried out at a slurry temperature of at least 70° C. or more preferably at a temperature of at least 80° C. It may be easier to control the alkali detoxification process if the temperature is below the boiling point of the slurry. Thus, in one embodiment the addition of Na(OH), Ca(OH)$_2$ and/or CaO in step b) is being carried out at a slurry temperature in the range of 60 to 100° C., such as 70 to 100° C., such as 80 to 100° C. or 70 to 90° C.

In step c) the temperature and pH is adjusted so that the conditions are suitable for the hydrolytic enzymes. Therefore the temperature is reduced below 60° C. and the pH is reduced below 7.0. The optimum pH and temperature differs between different enzymes. However, for some hydrolytic enzymes the optimal temperature is in the range of 40-60° C. and the optimal pH in a range of 3.0 to 7.0. For example the optimal temperature of the commercially available hydrolytic enzyme Cellic CTec2 is 45 to 50° C. and the optimal pH is about 5.0 to 5.5 Therefore, in a preferred embodiment, step c) comprises cooling the slurry from step b) to a temperature between 40 and 60° C. such as between 45 to 55° C., for example 45 to 50° C. In another preferred embodiment step c) comprises reducing the pH of the slurry to a pH in a range of 3.0 to 7.0 such as 4 to 6.5, for example 5.0 to 5.5.

Step d) involves addition of hydrolytic enzymes to the slurry from step c) and allowing the slurry to hydrolyze.

The hydrolytic enzymes may include at least one saccharification enzyme, which refers to at least one enzyme that can convert or hydrolyze cellulosic biomass into fermentable saccharides, such as monosaccharides and/or disaccharides and/or oligosaccharides. Such saccharification enzymes may be glycosidases, which hydrolyze polysaccharides. Examples of glycosidases include cellulose-hydrolyzing glycosidases, such as cellulases, endoglucanases, exoglucanases, cellobiohydrolases and β-glucosidases, hemicellulose hydrolyzing glycosidases, such as xylanases, endoxylanases, exoxylanases, β-xylosidases, arabinoxylanases, mannanases, galactanases, pectinases and glucuronases, and starch hydrolyzing glycosidases, such as amylases, α-amylases, β-amylases, glucoamylases, α-glucosidases and isoamylases, or any enzymes in the group of enzymes found in EC 3.2.1.x, such as EC 3.2.1.4, where EC is the Enzyme Commission number.

It is surprising that the enzymatic hydrolysis of cellulosic substrates in the presence of the liquid fraction obtained after pretreatment of a lignocellulose material can be enhanced by alkaline treatment. The underlying mechanism for this effect is not known at present. The inventors have also surprisingly discovered that only some bases seem to be suitable for the alkaline treatment. For example the inventors have demonstrated that conditioning with Na(OH) and Ca(OH)$_2$ increased the saccharification yield with about 20% while conditioning with ammonium hydroxide did not result in any improvement of the saccharification yield.

As well known by the skilled person, CaO reacts with water to form Ca(OH)$_2$. Ca(OH)$_2$ and CaO are particular suitable bases for the alkaline treatment since they are relatively cheap. One problem with using CaO or Ca(OH)$_2$ in the alkaline treatment is that the calcium ions derived from the calcium based base easily react with sulfate ions from the sulfuric acid from the pre-treatment liquid. This leads to formation of gypsum which could cause deposits and clog the equipment. The present inventors have realized that, in contrast to sulfuric acid, SO$_2$ or sulfurous acid does not give rise to substantial levels of sulfate ions and thus pre-treatment with SO$_2$ or sulfurous acid followed by alkaline treatment with Ca(OH)$_2$ and/or CaO is particularly suitable according to the present invention.

Accordingly, a second aspect of the invention relates to a method of enzymatic hydrolysis of a lignocellulosic material, comprising the steps of:
a) pretreating the lignocellulosic material using SO2 and/or sulfurous acid to obtain a slurry having a pH of less than 5;
b) adding Ca(OH)$_2$ and/or CaO to the slurry to increase its pH to at least 8;
c) reducing the pH of the slurry from step b) to below 7; and
d) adding hydrolytic enzymes to the slurry from c) and allowing the slurry to hydrolyze.

The embodiments of the first aspect apply to the second aspect mutatis mutandis.

According to one embodiment the method is for production of at least one target molecule from the lignocellulosic material and further comprises a step e) of utilizing the at least partly hydrolyzed slurry from step d) as a substrate for production of at least one target molecule. According to one embodiment the at least one target molecule is a fermentation product, and the step e) of utilizing the at least partly hydrolyzed slurry comprises subjecting the at least partly hydrolyzed slurry to fermentation.

In one embodiment, the fermentation is a simultaneous saccharification and fermentation (SSF) of a pretreated lignocellulosic material. A SSF process refers to a process in which enzymatic hydrolysis and fermentation is performed simultaneously in a fermentor. Thus, in a SSF process, fermentable saccharides are prepared directly in a fermentor by enzymatic hydrolysis of the pretreated lignocellulosic material, and the resulting saccharides are converted into a fermentation product. Further, the fermentation may be a consolidated bioprocess (CBP), in which the biocatalyst that convert the monosaccharides also produces the enzymes that hydrolyze the pretreated lignocellulosic material. In another embodiment, the hydrolysate that is subjected to fermentation is obtained from a separate, preceding step of enzymatic hydrolysis. Consequently, the enzymatic hydrolysis and the fermentation may be performed as two separate process steps (separate hydrolysis and fermentation, SHF). This may e.g. be advantageous if the fermentation reaction and the enzymatic reaction have different optimal temperatures. As an example, the temperature during enzymatic hydrolysis may be kept higher than the temperature during fermentation, thus facilitating the use of thermophilic enzymes.

In one embodiment fermentation is performed by a fermenting organism and the fermenting organism can for example be bacteria and/or yeast. In one embodiment the fermenting organism is yeasts from the genera *Saccharomyces*, *Pichia* or *Candida*. In one embodiment the fermenting organism is bacteria from the genera *Zymomonas* or *Escherichia*. Preferably, the fermenting organism may be wild type, mutant or recombinant *Saccharomyces cerevisiae*. Using *S. cerevisiae* for producing a fermentation product is advantageous since *S. cerevisiae* is well established with regard to industrial fermentation and provides for a high product yield. According to one embodiment the fermentation product is selected from alcohols, acids, alkanes, alkenes, aromatics, aldehydes, ketones, biopolymers, proteins, peptides, amino acids or vitamins. In one embodiment the fermentation product is selected from ethanol, butanol, acetic acid, butyric acid and succinic acid.

Besides of fermenting the sugars, the sugars can also be utilized as substrates in various other chemical and biochemical (e.g. enzymatic) methods for production of desired target compounds. By way of example, the sugars can be used in a thermochemical process to produce levulinic acid, which in turn is an intermediate in the synthesis of polymers, plastics and pharmaceuticals. It is also a precursor in the industrial production of other chemical commodities such as methyltetrahydrofuran, valerolactone, and ethyl levulinate. Therefore, according to one embodiment the at least one target molecule is levulinic acid.

As discussed above several different hydrolytic enzymes can be used in the methods according to the invention. According to one embodiment the addition of hydrolytic enzyme in step d) comprises the addition of at least one glycosidases such as a cellulose-hydrolyzing glycosidase, hemicellulose hydrolyzing glycosidase and/or a starch hydrolyzing glycosidase. In one embodiment at least one of the hydrolytic enzymes added in step d) is a cellulase, endoglucanase, exoglucanase, cellobiohydrolase, β-glucosidase, xylanase, endoxylanase, exoxylanase, β-xylosidase, arabinoxylanase, mannanase, galactanase, pectinase, glucuronase, amylase, α-amylase, β-amylase, glucoamylase, α-glucosidase, isoamylase, and/or any enzymes in the group of enzymes found in EC 3.2.1.x, such as EC 3.2.1.4, where EC is the Enzyme Commission number. In one embodiment at least one enzyme originates from a filamentous fungus, such as *Hypocrea jecorina*.

In one embodiment at least one endoglucanase, at least one exoglucanase and at least one β-glucosidase is added in step d). For example a combination of the commercial enzyme preparations Celluclast 1.5 L and Novozyme 188 can be added in step d)."

The method according to the invention is directed to treatment of lignocellulosic materials. The term lignocellulosic material includes material comprising cellulose, lignin and possibly hemicellulose. The lignocellulose material may for example be a forestry residue, such as wood (e.g. wood chips), sawmill or paper mill by products or an agricultural residue, e.g. corn stover/cobs, sugarcane bagass or wheat straw. Depending on the geographical location, wood, corn stover/cobs, wheat straw or sugarcane bagass may be available in large quantities, making them attractive as raw materials.

In one embodiment the dry matter content of the slurry in step a) is in the range of from 5 to 40% (w/v), such as from 8 to 30% (w/v), such as from 12 to 20% (w/v).

In the prior art washing of the slurry with water, which may comprise a chemical, has been described. For example Pan et al. describes that the enzymatic hydrolysis of a pretreated softwood with high residual lignin content can be enhanced by mild alkali extraction. This strategy is different from the concept of the present invention since the purpose is to remove lignin. Importantly this method described in Pan et al. is dependent of an extraction of the lignin and it is described that the pretreated material is washed extensively with water subsequent to the alkaline extraction. The present invention does not relate to decreasing the lignin content of a pretreated lignocellulosic biomass. Rather, the present invention is based on the surprising discovery that alkaline treatment of the pretreated slurry has a detoxifying effect on the enzymatic hydrolysis. Therefore the present invention does need a washing or extraction stage to remove lignin. In fact, such a washing is undesired since it may remove water soluble fermentable saccharides from the slurry and thus decrease the overall yield in the process. Also, such a washing may increase the fresh water consumption in the method. Thus, in one embodiment no washing of the slurry is performed prior to step d).

For the same reason as described above, in the method according to the present invention, no separation of pretreatment liquid from the solids is necessary prior to the hydrolysis step. Thus in one embodiment at least 50%, preferably at least 90% or 95% of the liquid in the pretreated slurry from step a) is present during the enzymatic hydrolysis step d). In one embodiment, 100% of the liquid is present. The percentage of liquid may, depending on the circumstances, be calculated by weight or by volume.

Other documents in the prior art, such as WO2005/099854, discloses acidic pre-treatment of a lignocellulosic feedstock followed by an adjustment of the pH to 4.0-6.0. Since the pH is not raised to at least 8, the pH adjustment described in WO2005/099854 will not be sufficient to have a detoxifying effect on the enzymatic hydrolysis.

A third aspect of the invention relates to a method of producing at least one target molecule comprising the steps of:
a) pretreating a lignocellulosic material to obtain a slurry having a pH of less than 6;
b) adding Na(OH), Ca(OH)$_2$ and/or CaO to the slurry to increase its pH to at least 8;
c) reducing the pH of the slurry to below 7;
d) adding hydrolytic enzymes to the slurry from c) and subjecting the slurry to enzymatic hydrolysis to obtain an at least partly hydrolyzed slurry; and
e) utilizing the at least partly hydrolyzed slurry from step d) as a substrate in a fermentation process for production of at least one fermentation product, wherein the enzymatic hydrolysis in step d) and the fermentation process in step e) are performed separately in a separate hydrolysis and fermentation (SHF) process.

A fourth aspect of the present invention relates to use of NaOH, Ca(OH)$_2$ or CaO for improving the enzymatic hydrolysis of a lignocellulose-derived slurry derived from dilute acid pretreatment. In one embodiment the dilute acid pretreatment is a pretreatment using SO$_2$ and/or sulfurous acid.

The embodiments of the first and second aspects apply to the third and fourth aspects mutatis mutandis.

EXAMPLES

Pretreatment of unbarked wood chips of Norway spruce (*Picea abies*) was performed in continuous mode in a 30-liter reactor. Sulfur dioxide was used as catalyst (one kg of sulfur dioxide per 40 kg of wood chips). The pretreatment was carried out at 203° C. for 5 min. After the pretreatment, the pH of the slurry was 2, and the dry matter content was 13.8% (w/w). The pretreated material was stored at 4° C. until further use.

The pretreatment liquid, i.e. the liquid fraction of the pretreated spruce slurry, was obtained by filtration. The content of monosaccharides, aliphatic acids, and furan aldehydes in the pretreatment liquid were determined by using high-performance liquid chromatography (HPLC) (MoRe Research, Örnsköldsvik, Sweden) and the concentrations were: 26.5 g/l mannose, 29.0 g/l glucose, 12.5 g/l xylose, 5.8 g/l galactose, 3.1 g/l arabinose, 5.8 g/l acetic acid, <0.1 g/l formic acid, 1.3 g/l levulinic acid, 2.3 g/l 5-hydroxymethylfurfural (HMF), and 1.8 g/l furfural.

The total concentration of phenols in the pretreatment liquid was estimated to 6.6 g/l by using a spectrophotometric method (Singleton et al. 1999) based on the Folin and Ciocalteu reagent (Sigma-Aldrich, St Louis, Mo., USA). Vanillin was used as the standard. Before phenol determinations, the pH of the samples was adjusted to 5.2 using 37% HCl or a 5 M solution of NaOH.

Alkaline Treatment

Prior to alkaline treatment, portions (72.5 g) of the slurry of pretreated spruce [13.8% (w/w) dry weight] were diluted with deionized water (27.5 g) to achieve a dry-matter content of 10.0% (w/w). The pretreatment liquid was treated with alkali without any cellulosic substrate being present. The spruce slurry and the pretreatment liquid were treated with NH$_4$OH, NaOH, and Ca(OH)$_2$ as summarized in Table 1.

In a first set of experiments the treatment conditions were pH 9 and 55° C. for the NH$_4$OH treatment, pH 9 and 80° C. for the NaOH treatment, and pH 11 and 30° C. for the Ca(OH)$_2$ treatment (Table 1). The samples were kept under alkaline conditions for 3 h with magnetic stirring. After completion of the alkaline treatment, the pH of the samples was adjusted to 5.2 using HCl (37%). For comparison, deionized water was added to untreated slurry and pretreatment liquid samples so that the dilution was the same as for the alkali-treated samples. The pH of the untreated slurry and the pretreatment liquid was adjusted to 5.2 using the 5 M NaOH solution. After dilutions with water, alkali treatments and pH adjustments, the content of slurry was 69%

(w/w) and the dry-matter content was 9.5% (w/w), while the content of pretreatment liquid was 94% (w/w).

In a second set of experiments performed with the pretreated spruce slurry, all alkaline treatments were carried out at pH 9 and 80° C. (Table 1). Dilutions and pH adjustments were performed as in the first set of experiments.

Enzymatic Hydrolysis

Hydrolysis experiments with the pretreatment liquid were performed by adding a cellulosic substrate, Avicel PH 101 (a preparation of microcrystalline cellulose purchased from Sigma-Aldrich). Avicel was added to the pretreatment liquid after the pH had been adjusted to 5.2, as described above.

Two commercial enzyme preparations were used in the hydrolysis experiments, the *Trichoderma reesei* (*Hypocrea jecorina*) cellulase preparation Celluclast 1.5 L and Novozyme 188. Novozyme 188 was added to assure that sufficient amounts of β-glucosidase (cellobiase) were present in the reaction mixtures. The enzyme preparations were purchased from Sigma-Aldrich and the stated activities were: Celluclast 1.5 L, 700 endoglucanase units (EGU)/g; Novozyme 188, 250 cellobiase units (CBU)/g.

Enzymatic hydrolysis experiments were conducted in 100-ml E-flasks containing reaction mixtures with a total mass of 25 g. The reaction mixtures with slurry consisted of 24.5 g alkali-treated or untreated slurry, pH 5.2, and 0.5 g of an enzyme cocktail consisting of equal amounts (w/w) of Celluclast 1.5 L and Novozyme 188. The content of slurry in the final reaction mixtures was 68% (w/w), the dry matter content was 9.3% (w/w), and the content of enzyme cocktail was 2% (w/w). The reaction mixtures with pretreatment liquid consisted of 22 g alkali-treated or untreated pretreatment liquid, pH 5.2, 2.5 g of Avicel, and 0.5 g of the enzyme cocktail. The content of pretreatment liquid in the final reaction mixtures was 83% (w/w) and the content of enzyme cocktail was 2% (w/w). Duplicate experiments were performed for each hydrolysis reaction.

The E-flasks, which were covered with parafilm and aluminum foil, were incubated for 72 h at 45° C. in an orbital shaker (Ecotron incubator shaker, Infors, Bottmingen, Swizerland) set at 170 rpm. During the hydrolysis, 100 µl samples were collected, typically after 0, 24, 48, and 72 h. In the beginning and at the end of the hydrolysis experiments (i.e at 0 and 72 h), 1 ml samples were also taken. The samples were chilled on ice, and were then centrifuged at 14,100 g for 5 min. The supernatants were collected and used for sugar analysis.

Glucose Analysis

The glucose concentration of the samples that were collected during the hydrolysis experiments was determined using a glucometer (Glucometer Elite XL, Bayer AG, Leverkusen, Germany). Each sample was analyzed twice. Analyses of the sugar content of samples collected at 0 and 72 h were also performed using ion chromatography (IC) and high-performance liquid chromatography (HPLC) (MoRe Research). The glucometer values were corrected using data obtained by chromatographic determination of glucose.

Results

The effects of alkaline treatment on the enzymatic hydrolysis of two cellulosic substrates, pretreated spruce wood and Avicel, were investigated in experiments with three different types of alkali; calcium hydroxide, sodium hydroxide, and ammonium hydroxide. The experimental series with pretreated wood and Avicel differ in the sense that Avicel was never exposed to alkaline conditions, and any improvements observed with Avicel must therefore be attributed to effects of alkali on the pretreatment liquid rather than on the solid phase. The experiments with spruce wood slurry indicate the effect of alkaline treatment on the saccharification of a realistic lignocellulosic substrate, which besides cellulose also contains other components, notably lignin.

Figure 1B:
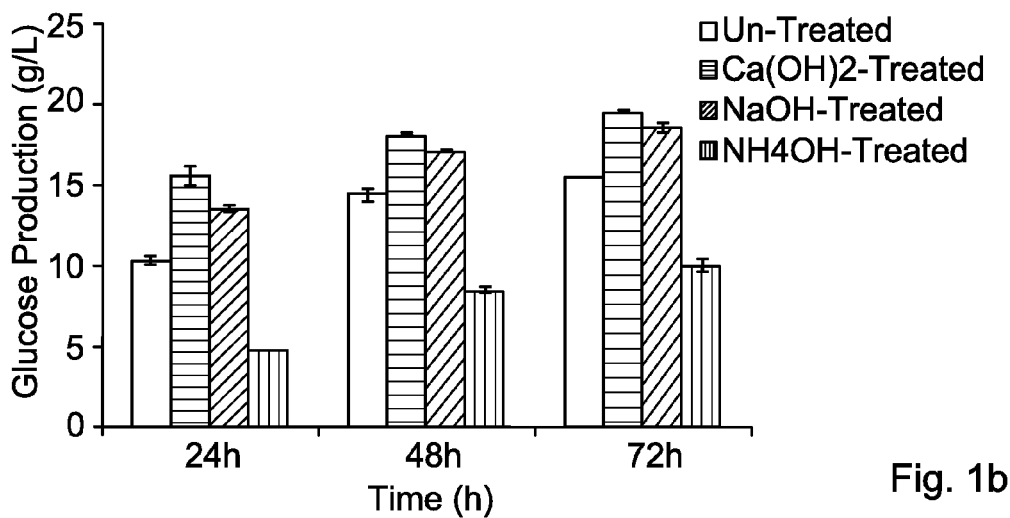
FIG. 1b
The Y-axis shows glucose production (g/l) during 72 h of enzymatic hydrolysis of cellulose (Avicel) in alkali-treated and untreated pretreatment liquid. The treatment conditions were: NH4OH, pH 9, 55° C., 3 h; NaOH, pH 9, 80° C., 3 h; Ca(OH)2, pH 11, 30° C., 3 h. Error bars show the standard deviations of four measurements.

The results obtained from the first set of experiments with spruce wood slurry and alkaline treatments are shown in FIG. 1a. After 72 h, conditioning with calcium hydroxide and sodium hydroxide increased the saccharification yield with 17 and 20%, respectively. Conditioning with ammonium hydroxide did, however, not result in any improvement. When the same treatment conditions were used for pretreatment liquid that was subsequently mixed with Avicel (FIG. 1b), calcium hydroxide and sodium hydroxide again gave improved saccharification yield (26 and 20% improvement after 72 h for calcium hydroxide and sodium hydroxide, respectively).

Figure 1C:
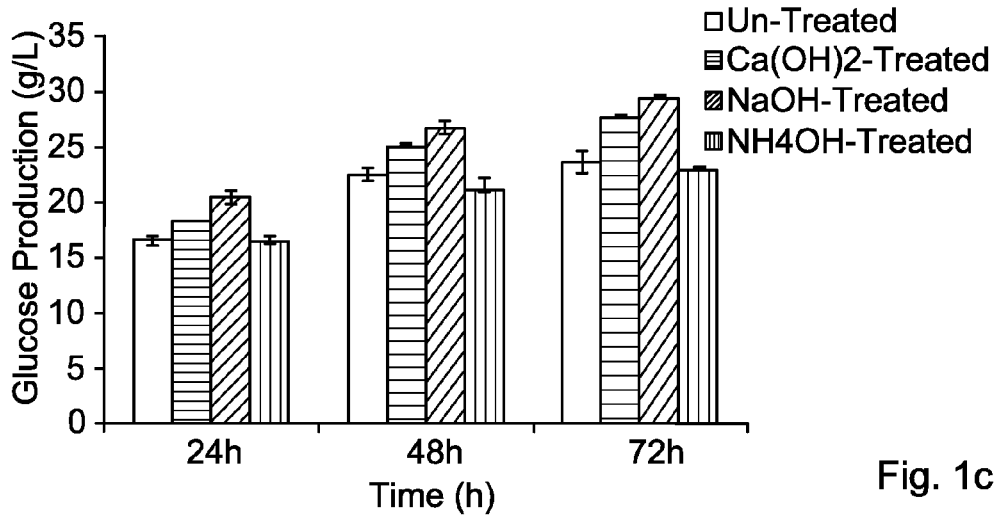
FIG. 1c
The Y-axis shows glucose production (g/l) during 72 h of enzymatic hydrolysis of alkali-treated and untreated spruce slurry. The treatment conditions were: NH4OH, pH 9, 80° C., 3 h; NaOH, pH 9, 80° C., 3 h; Ca(OH)2, pH 9, 80° C., 3 h. Error bars show the standard deviations of four measurements.

In a second set of experiments with the spruce wood slurry, all alkaline treatments were carried out in the same way, pH 9 and 80° C., (FIG. 1c). After 72 h, calcium hydroxide and sodium hydroxide treatments resulted in improvements of the saccharification yield amounting to 17% and 25%, respectively. It has thus been shown that an increased temperature may compensate for a decreased pH. Accordingly, lower amounts of base may be added if the process is performed at a higher temperature. As the pretreatment is normally performed at an elevated temperature, such as about 200° C., no extra heating step will normally be required for reaching the appropriate temperature in the industrial setting. The saccharification yield obtained with ammonium hydroxide treatment was comparable to that of the untreated sample (FIG. 1c). In summary, treatments with calcium hydroxide or sodium hydroxide resulted in improvements in the range 17-26%, while ammonium hydroxide treatment did not improve the situation. The ammonium hydroxide treatment shown in FIG. 1c was more powerful than the treatments shown in FIGS. 1 and 2 in the sense that the pH was the same while the temperature was higher (80° C. rather than 55° C.).

TABLE 1

Summary of alkaline treatments used in the experiments.

| Sample No | Medium | Alkali | pH | Temperature | Time (h) |
|---|---|---|---|---|---|
| 1 | S[a] and P[b] | NH$_4$OH | 9 | 55° C. | 3 |
| 2 | S | NH$_4$OH | 9 | 80° C. | 3 |
| 3 | S and P | NaOH | 9 | 80° C. | 3 |
| 4 | S and P | Ca(OH)$_2$ | 11 | 30° C. | 3 |
| 5 | S | Ca(OH)$_2$ | 9 | 80° C. | 3 |
| 6 | S and P | Untreated | — | — | — |

[a]S, Spruce slurry;
[b]P, Pretreatment liquid

REFERENCES

Singleton V, et al. "Analysis of total phenols and other oxidation substrates and antioxidants by means of folin-ciocalteu reagent" (1999) *Methods Enzymol.* Vol 299, pages 152-178.

Pan X et al "Strategied to enhance the enzymatic hydrolysis of pretreated softwood with high residual ligning content" (2005), *Applied Biochemistry and Biotechnology* vol 124, pages 1069-1079

Alriksson et al. "Ammonium hydroxide detoxification of spruce acid hydrolysates" (2005) *Applied Biochemistry and Biotechnology* 121-124:911-22.

Alriksson et al "Optimal conditions for alkaline detoxification of dilute-acid lignocellulose hydrolysates" (2006) vol 130 pages 599-611.

Alvira et al. "Pretreatment technologies for an efficient bioethanol production process based on enzymatic hydrolysis: A review." (2010) vol 101, pages 4851-61.

Harmsen et al. "Literature review of physical and chemical pretreatment processes for lignocellulosic biomass" (2010) ISBN: 978-90-8585-757-0.

The invention claimed is:

1. A method of enzymatic hydrolysis of a lignocellulosic material, comprising the steps of:
   a) pretreating the lignocellulosic material with an acid to obtain a slurry having a pH of less than 6;
   b) adding NaOH, $Ca(OH)_2$ and/or CaO to the slurry to increase its pH to at least 8, said addition being carried out at a slurry temperature of at least 70° C., wherein the alkaline treatment has a detoxifying effect on the enzymatic hydrolysis of step d);
   c) reducing the pH of the slurry to below 7 and optionally cooling the slurry from step b) to a temperature below 60° C.; and
   d) adding hydrolytic enzymes that can hydrolyze cellulosic biomass into fermentable saccharides to the slurry from step c) and allowing the enzymes to hydrolyze the slurry to obtain slurry containing fermentable saccharides,
   wherein no washing of the slurry of a), b), or c) is performed prior to step d).

2. A method of enzymatic hydrolysis of a lignocellulosic material, comprising the steps of:
   a) pretreating the lignocellulosic material using $SO_2$ and/or sulfurous acid to obtain a slurry having a pH of less than 5;
   b) adding $Ca(OH)_2$ and/or CaO to the slurry to increase its pH to at least 8, wherein the alkaline treatment has a detoxifying effect on the enzymatic hydrolysis of step d);
   c) reducing the pH of the slurry from step b) to below 7; and
   d) adding hydrolytic enzymes that can hydrolyze cellulosic biomass into fermentable saccharides to the slurry from c) and allowing the enzymes to hydrolyze the slurry to obtain slurry containing fermentable saccharides,
   wherein no washing of the slurry of a), b), or c) is performed prior to step d).

3. A method of producing at least one target molecule comprising the steps of:
   a) pretreating a lignocellulosic material with an acid to obtain a slurry having a pH of less than 6;
   b) adding NaOH, $Ca(OH)_2$ and/or CaO to the slurry to increase its pH to at least 8, wherein the alkaline treatment has a detoxifying effect on the enzymatic hydrolysis of step d);
   c) reducing the pH of the slurry to below 7;
   d) adding hydrolytic enzymes that can hydrolyze cellulosic biomass into fermentable saccharides to the slurry from c) and subjecting the slurry to enzymatic hydrolysis to obtain an at least partly hydrolyzed slurry containing fermentable saccharides; and
   e) utilizing the at least partly hydrolyzed slurry from step d) as a substrate in a fermentation process for production of at least one fermentation product,
   wherein the enzymatic hydrolysis in step d) and the fermentation process in step e) are performed separately and wherein no washing of the slurry of a), b), or c) is performed prior to step d).

4. The method according to claim 1, wherein said method is for production of at least one target molecule from the lignocellulosic material and further comprising a step e) of utilizing the at least partly hydrolyzed slurry from step d) as a substrate for the production of at least one target molecule.

5. The method according to claim 4 wherein the at least one target molecule is a fermentation product, and the step e) of utilizing the at least partly hydrolyzed slurry comprises subjecting the at least partly hydrolyzed slurry to fermentation.

6. The method according to claim 5 wherein the enzymatic hydrolysis in step d) and the fermentation in step e) are performed separately in a separate hydrolysis and fermentation process.

7. The method according to claim 5 wherein the enzymatic hydrolysis in step d) and the fermentation in step e) are performed simultaneously in a simultaneous saccharification and fermentation process.

8. The method according to claim 3, wherein the fermentation is performed by yeast.

9. The method according to claim 3, wherein the fermentation product is selected from an alcohol, an acid, an alkane, an alkene, an aromatic, an aldehyde, a ketone, a biopolymer, a protein, a peptide, an amino acid or a vitamin.

10. The method according to claim 1, wherein the addition of hydrolytic enzymes in step d) comprises the addition of at least one glycosidase.

11. The method according to claim 1, wherein the lignocellulosic material is a wood material or an agricultural residue.

12. The method according to claim 1, wherein at least 90% of the liquid in the pretreated slurry from step a) is present during the enzymatic hydrolysis step d).

13. The method according to claim 10, wherein the glycosidase is a cellulose-hydrolyzing glycosidase, a hemicellulose hydrolyzing glycosidase and/or a starch hydrolyzing glycosidase.

14. The method according to claim 2, wherein the addition of hydrolytic enzymes in step d) comprises the addition of at least one glycosidase.

15. The method according to claim 2, wherein the lignocellulosic material is a wood material or an agricultural residue.

16. The method according to claim 14, wherein the glycosidase is a cellulose-hydrolyzing glycosidase, a hemicellulose hydrolyzing glycosidase and/or a starch hydrolyzing glycosidase.

17. The method according to claim 3, wherein the addition of hydrolytic enzymes in step d) comprises the addition of at least one glycosidase.

18. The method according to claim 3, wherein the lignocellulosic material is a wood material or an agricultural residue.

19. The method according to claim 17, wherein the glycosidase is a cellulose-hydrolyzing glycosidase, a hemicellulose hydrolyzing glycosidase and/or a starch hydrolyzing glycosidase.

* * * * *

UNITED STATES PATENT AND TRADEMARK OFFICE
CERTIFICATE OF CORRECTION

PATENT NO. : 9,512,454 B2  Page 1 of 1
APPLICATION NO. : 14/123556
DATED : December 6, 2016
INVENTOR(S) : Jönsson et al.

It is certified that error appears in the above-identified patent and that said Letters Patent is hereby corrected as shown below:

In the Specification
Column 5, Line 14: Please correct "3-glucosidases," to read -- β-glucosidases, --
Column 5, Line 16: Please correct "3-xylosidases," to read -- β-xylosidases, --

Signed and Sealed this
Sixth Day of June, 2017

Michelle K. Lee
*Director of the United States Patent and Trademark Office*